(12) United States Patent
Yeghiazarians et al.

(10) Patent No.: US 9,084,761 B2
(45) Date of Patent: Jul. 21, 2015

(54) USE OF INTERLEUKIN-15 TO TREAT CARDIOVASCULAR DISEASES

(75) Inventors: Yerem Yeghiazarians, San Francisco, CA (US); Joel S. Karliner, San Francisco, CA (US); Andrew Boyle, San Francisco, CA (US); Franca Angeli, San Francisco, CA (US); Jean-Philippe Coppe, San Francisco, CA (US)

(73) Assignees: The Regents of the University of California, Oakland, CA (US); The United States of America Represented by the Department of Veterans Affairs, Washington, DC (US)

( * ) Notice: Subject to any disclaimer, the term of this patent is extended or adjusted under 35 U.S.C. 154(b) by 113 days.

(21) Appl. No.: 13/809,154

(22) PCT Filed: Jul. 8, 2011

(86) PCT No.: PCT/US2011/043447
§ 371 (c)(1),
(2), (4) Date: May 30, 2013

(87) PCT Pub. No.: WO2012/006585
PCT Pub. Date: Jan. 12, 2012

(65) Prior Publication Data
US 2013/0259827 A1    Oct. 3, 2013

Related U.S. Application Data

(60) Provisional application No. 61/363,163, filed on Jul. 9, 2010.

(51) Int. Cl.
| | |
|---|---|
| A61K 38/20 | (2006.01) |
| A61P 9/10 | (2006.01) |
| A61P 39/06 | (2006.01) |
| A61P 25/00 | (2006.01) |
| A61K 35/28 | (2015.01) |
| C07K 14/54 | (2006.01) |

(52) U.S. Cl.
CPC ............ *A61K 38/2086* (2013.01); *A61K 35/28* (2013.01); *C07K 14/5443* (2013.01)

(58) Field of Classification Search
None
See application file for complete search history.

(56) References Cited

U.S. PATENT DOCUMENTS

2010/0021421 A1    1/2010 Galipeau et al.

FOREIGN PATENT DOCUMENTS

WO    WO 2008014612 A1 *    2/2008

OTHER PUBLICATIONS

International Preliminary Report on Patentability dated Jan. 15, 2013, for PCT Application No. PCT/US2011/043447 filed on Jul. 8, 2011, 6 pages.
International Search Report and Written Opinion mailed on Mar. 7, 2012, for PCT Application No. PCT/US2011/043447 filed on Jul. 8, 2011, 9 pages.
Micieli et al. (2009). "Safety and efficacy of alteplase in the treatment of acute ischemic stroke," Vascular Health and Risk Management, 5: 397-409.
Rubboli (2008). "Efficacy and safety of low-molecular-weight heparins as an adjunct to thrombolysis in acute ST-elevation myocardial infarction," Current Cardiology Reviews, 4(1): 63-71.
Yeghiazarians et al. (2009). "Injection of bone marrow cell extract into infarcted hearts results in functional improvement comparable to intact cell therapy," Molecular Therapy, 17(7): 1250-1256.
Yeghiazarians et al. (2014). "IL-15: a novel prosurvival signaling pathway in cardiomyocytes," J Cardiovasc Pharmacol, 63(5): 406-411.
Alvarez et al. (2002) "Effects of interleukin-15 (IL-15) on adipose tissue mass in rodent obesity models: evidence for direct IL-15 action on adipost tissue," Biochim Biophys Acta, 1570: 33-37.
Gómez-Nicola et al. (2011) "Interleukin-15 regulates proliferation and self-renewal of adult neural stem cells," Mol Biol Cell, 22: 1960-1970.

\* cited by examiner

*Primary Examiner* — Zachary Howard
(74) *Attorney, Agent, or Firm* — Morrison & Foerster LLP

(57) ABSTRACT

The present disclosure relates generally to the field of cardiovascular diseases. In particular, the present disclosure relates to methods and compositions for treating cardiovascular diseases by administration of a cytokine alone, or in conjunction with other therapeutic agents.

20 Claims, 2 Drawing Sheets

Nx: normoxia; veh: vehicle; H/R – hypoxia

Nx: normoxia; Hx: hypoxia (N=8/group)

SEQUENCE LISTING

```
<160> NUMBER OF SEQ ID NOS: 1

<210> SEQ ID NO 1
<211> LENGTH: 113
<212> TYPE: PRT
<213> ORGANISM: Homo sapiens

<400> SEQUENCE: 1

Trp Val Asn Val Ile Ser Asp Leu Lys Lys Ile Glu Asp Leu Ile Gln
1               5                   10                  15

Ser Met His Ile Asp Ala Thr Leu Tyr Thr Glu Ser Asp Val His Pro
            20                  25                  30

Ser Cys Lys Val Thr Ala Met Lys Cys Phe Leu Leu Glu Leu Gln Val
        35                  40                  45

Ile Ser Leu Glu Ser Gly Asp Ala Ser Ile His Asp Thr Val Glu Asn
    50                  55                  60

Leu Ile Ile Leu Ala Asn Asn Ser Leu Ser Ser Asn Gly Asn Val Thr
65                  70                  75                  80

Glu Ser Gly Cys Lys Glu Cys Glu Glu Leu Glu Glu Lys Asn Ile Lys
                85                  90                  95

Glu Phe Leu Gln Ser Phe Val His Ile Val Gln Met Phe Ile Asn Thr
            100                 105                 110

Ser
```

USE OF INTERLEUKIN-15 TO TREAT CARDIOVASCULAR DISEASES

CROSS-REFERENCE TO RELATED APPLICATIONS

This application is a U.S. National Phase of PCT/US2011/043447, filed Jul. 8, 2011, which claims the benefit under 35 USC 119(e) of U.S. Provisional Patent Application No. 61/363,163, filed Jul. 9, 2010, each of which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643662001300SEQLISTING.txt, date recorded: Jan. 8, 2013, size: 2 KB).

FIELD

The present disclosure relates generally to the field of cardiovascular diseases. In particular, the present disclosure relates to methods and compositions for treating cardiovascular diseases by administration of a cytokine alone, or in conjunction with other therapeutic agents.

BACKGROUND

Cardiovascular diseases including myocardial infarction (MI), ischemic cardiomyopathy, congestive heart failure and stroke remain prominent health challenges worldwide. Despite therapeutic advances, there are currently no approaches in clinical practice that replace myocardial scars with functioning contractile tissue (Losordo et al., Circ, 109: 2692-2697, 2004; Wollert and Drexler, Circ Res, 96:151-163, 2005; and Rosensweig, N Eng J Med, 355:1274-1277, 2006), or dead neurons with functioning cells. Thus, the art is in need of therapeutic regimens for reducing the size of the infarct to improve cardiac function. In addition, other cardiovascular end organs (e.g., brain and spinal cord) would benefit from such therapeutic regimens.

SUMMARY

The present disclosure relates generally to the field of cardiovascular diseases. In particular, the present disclosure relates to methods and compositions for treating cardiovascular diseases by administration of a cytokine alone, or in conjunction with other therapeutic agents.

The present disclosure provides the use of IL-15 for the treatment of ischemic cardiovascular disease in a patient. In some embodiments, the IL-15 is administered in combination with an additional agent derived from a bone marrow extract. In some embodiments, the ischemic cardiovascular disease is ischemic heart disease (e.g., myocardial infarction). In some embodiments, the ischemic cardiovascular disease is stroke. The present disclosure also provides methods for the treatment of ischemic cardiovascular disease, comprising: administering a composition comprising interleukin-15 (IL-15) to a patient in need thereof. In some embodiments, the IL-15 is administered in combination with an additional agent derived from a bone marrow extract. In some preferred embodiments, the ischemic cardiovascular disease is an ischemic heart disease selected from the group consisting of coronary heart disease, coronary artery disease, acute coronary syndrome, angina pectoris, myocardial infarction (MI), ischemic cardiomyopathy, and congestive heart failure. In some embodiments, the ischemic cardiovascular disease is MI. In some embodiments, the composition comprises the IL-15 in an amount effective to reduce scarring following the myocardial infarction, increase left ventricular ejection fraction following the myocardial infarction, and/or enhance mycardial remodeling following the myocardial infarction. In some embodiments, the methods further comprise administering to the patient an agent used in the routine treatment of myocardial infarction, either sequentially or simultaneously with the composition comprising IL-15. In some embodiments, the agent used in the routine treatment of myocardial infarction is selected from the group consisting of thrombolytic agents, glycoprotein IIb-IIIa, other platelet inhibitors, calcium channel blockers, anti-arrhythmics, heparin, nitrates, beta-blockers, angiotensin receptor blockers, and angiotensin converting enzyme inhibitors. In some embodiments the ischemic cardiovascular disease is stroke. In some embodiments, the composition comprises the IL-15 in an amount effective to decrease negative consequences of stroke. In some embodiments, the methods further comprise administering to the patient an agent used in the routine treatment of stroke, either sequentially or simultaneously with the composition comprising IL-15. In some embodiments, the agent used in the routine treatment of stroke is selected from the group consisting of thrombolytic agents, glycoprotein IIb-IIIa, other platelet inhibitors, calcium channel blockers, anti-arrhythmics, heparin, nitrates, beta-blockers, angiotensin receptor blockers, and angiotensin converting enzyme inhibitors.

In addition, the present disclosure provides pharmaceutical compositions comprising isolated IL-15 and an agent used in the routine treatment of myocardial infarction or stroke. In some embodiments, the agent used in the routine treatment of myocardial infarction or stroke is selected from the group consisting of thrombolytic agents, glycoprotein IIb-IIIa, other platelet inhibitors, calcium channel blockers, anti-arrhythmics, heparin, nitrates, beta-blockers, angiotensin receptor blockers, and angiotensin converting enzyme inhibitors. In some embodiments, the pharmaceutical composition further comprises an additional agent derived from a bone marrow extract.

Moreover, the present disclosure provides methods of protecting cardiomyocytes from hypoxia-induced cell death, comprising contacting the cardiomyocytes with a composition comprising IL-15 so as to increase viability of the cardiomyocytes after exposure to hypoxic conditions. In some embodiments, the contacting is in vitro or ex vivo. In some embodiments in which the contacting is ex vivo, the cardiomyocytes are part of a mammalian heart harvested for transplantation. In other embodiments, the contacting is in vivo. In some embodiments in which the contacting is in vivo, the hypoxic conditions comprise a myocardial infarction. In some embodiments in which the contacting is in vivo, the contacting comprises administration of the composition comprising IL-15 to a mammalian subject by parenteral injection. In some preferred embodiments the parenteral injection is by intra-venous (IV) injection or by ultrasound-guided injection proximal to the myocardial infarct. In some embodiments, the composition further comprises an additional agent derived from a bone marrow extract.

Additionally, the present disclosure provides methods of protecting neurons from hypoxia-induced cell death, comprising contacting the neurons with a composition comprising IL-15 so as to increase viability of the neurons after exposure to hypoxic conditions. In some embodiments, the contacting is in vitro or ex vivo. In some embodiments, the neurons are part of a mammalian brain or spinal cord harvested for transplantation. In some embodiments, the contacting is in vivo. In some embodiments, the hypoxic conditions comprise a stroke. In some embodiments, the contacting comprises administration of the composition comprising IL-15 to a mammalian subject by intravenous injection or by ultrasound-guided injection proximal to the stroke. In some embodiments, the composition comprises an additional agent derived from a bone marrow extract

BRIEF DESCRIPTION OF THE DRAWINGS

FIG. 1A illustrates HL-1 (cell line derived from a mouse atrial cardiomyocyte tumor) cell viability as determined by MTT assay after hypoxia and reperfusion in the presence or absence of IL-15. There were significant differences in levels of cell viability between hypoxic control cells and cells incubated in the presence of 80 ng IL-15 (p=0.02 and p=0.05 respectively). FIG. 1B illustrates primary adult mouse cardiomyocyte viability as determined by cell counting after trypan blue staining after hypoxia and reperfusion in the presence or absence of IL-15. There were significant differences in levels of cell viability between hypoxic control cells and cells incubated in the presence of 5 ng and 20 ng IL-15.

DEFINITIONS

Figure 1A:
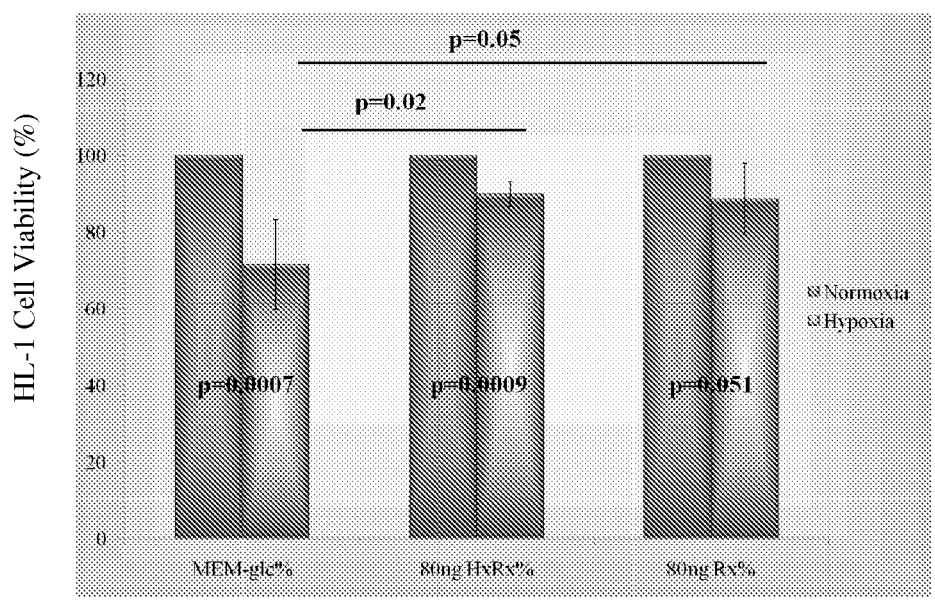
FIG. 1A-1B illustrates the protective effect of interleukin-15 (IL-15) on hypoxia-induced death of cardiomyocytes. Hypoxia (H/R veh) decreases cell viability (y-axis) as compared to normoxic conditions (Nx).

To facilitate an understanding of the embodiments disclosed herein, a number of terms and phrases are defined below. The practice of the present disclosure will employ, unless otherwise indicated, conventional techniques of clinical medicine, which are within the skill of the art. Such techniques are exemplified in Braunwald et al. (ed.), In "Heart Disease—A Textbook of Cardiovascular Medicine," 6th edition, W.B. Saunders Company, Philadelphia, Pa., Chapter 35, 2001; and Crawford (ed.), In "Current Diagnosis and Treatment of Cardiology," 2nd edition, Lange Medical Books/McGraw Hill, New York, N.Y., Chapter 5, 2003.

As used herein, the singular form "a", "an", and "the" includes plural references unless indicated otherwise. For example, "a" symptom includes one or more or more symptoms.

The terms "interleukin-15" and "IL-15" as used herein, refer to a cytokine known to have many biological activities in common with interleukin-2 (Grabstein et al., Science, 264: 965-968, 1994). IL-2 like activities include activities such as regulation of T cell and natural killer cell activation and proliferation). IL2RB and IL2RG, but not IL2RA, transduce signals by IL15 in addition to IL2 (Giri et al., EMBO J, 13:2822-2830, 1994). The terms "interleukin-15" and "IL-15" refer to the human IL-15 gene, cDNA and its gene product, as well as its mammalian counterparts. The cDNA sequence of human IL-15 is set forth as GENBANK Accession No. NM_000585.3, while the amino acid sequence of the mature form of human IL-15 is provided below:

```
                                           (SEQ ID NO: 1)
W VNVISDLKKI EDLIQSMHID ATLYTESDVH PSCKVTAMKC

FLLELQVISL ESGDASIHDT VENLIILANN SLSSNGNVTE

SGCKECEELE EKNIKEFLQS FVHIVQMFIN TS.
```

The terms "subject" and "patient" as used herein, refer to a mammalian subject, which in preferred embodiments is a human subject.

The term "ischemic heart disease" as used herein is to be understood as comprising any heart disease in which an insufficient blood supply to one or more regions of the myocardium occurs. Similarly, the term "ischemic cardiovascular disease" as used herein is to be understood as comprising any heart or neurologic disease in which an insufficient blood supply to one or more regions of the myocardium occurs or central nervous system (brain and/or spinal cord) occurs.

As used herein, the term "treatment" refers to an approach for obtaining beneficial or desired clinical results. For purposes of this disclosure, beneficial or desired clinical results include, but are not limited to, one or more of the following: ameliorating one or more symptoms associated with acute myocardial infarction, cardioprotection, reduction in infarct size, reduction in reperfusion injury, one or more diagnostic indicators in acceptable clinical ranges, reduction in frequency of interventional therapies, delay in cardiovascular disease progression, such as but not limited to congestive heart failure, and improvement in quality of life. Beneficial or desired clinical results also include minimizing the negative consequences of stroke or spinal cord injury.

As used herein, the term "prevention" refers to a reduction and/or delay in occurrence or reoccurrence of acute myocardial infarction or neurologic event in a subject at risk for an acute myocardial infarction or stroke as compared to a subject who is not determined to be at risk. A subject at risk includes, but is not limited to, a subject with a family history of hypertension, cardiovascular disease or congestive heart failure, stroke or combinations thereof. By way of example, subjects in need of the treatment methods described herein for acute myocardial infarction or stroke may be administered a preventive maintenance therapy by the methods described herein.

The term "ameliorating a symptom" includes a shortening or reduction in duration of a symptom, attenuation of a symptom, abolishment of the symptom or a delay in development or reoccurrence of the symptom. Symptoms of an acute myocardial infarction (AMI) may include, but are not limited to, ischemic symptoms, such as for example, chest, epigastric, arm, wrist or jaw discomfort and/or pain; nausea; vomiting; weakness; dizziness; palpitations; cold perspiration; dyspnea; syncope and/or diaphoresis (see, e.g., Braunwald, 2001 supra; and Crawford, 2003, supra). Symptoms of stroke may include but are not limited to numbness, weakness, difficulty speaking or swallowing, hearing loss, and combinations thereof.

"Cardioprotection" includes, but is not limited to, prevention, inhibition or reduction of myocardial cell necrosis resulting from an acute myocardial infarction and/or prevention, inhibition or reduction of myocardial cell damage. Similarly, "cardioneuroprotection" includes, but is not limited to, prevention, inhibition or reduction of myocardial and/or neuronal cell necrosis resulting from an acute myocardial infarction and/or stroke. As such the term "cardioneuroprotection" encompasses the prevention, inhibition or reduction of myocardial and/or neuronal cell damage.

"Diagnostic indicators" include, but are not limited to, clinical symptoms and imaging, including the rise and fall in biochemical markers indicative of myocardial cells becoming necrotic, such as for example, but not limited to, troponin and myocardial muscle creatinine kinase enzyme (CK-MB); development of pathologic Q waves on an electrocardiogram (ECG) and/or ST segment elevation or depression on an ECG (see, e.g., Braunwald, 2001 supra; and Crawford, 2003, supra).

An "effective amount" is generally an amount sufficient to effect beneficial or desired clinical results including, but not limited to, one or more of the following: ameliorating one or more symptoms associated with acute myocardial infarction and/or stroke; cardioprotection, cardioneuroprotection, neuroprotection, reduction in infarction size, reduction in reperfusion injury, one or more diagnostic indicators in acceptable clinical ranges and/or improvement in quality of life.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for parenteral administration are phosphate buffered saline or normal (0.9%) saline. Compositions comprising such carriers are formulated by well known conventional methods (see, e.g., Gennaro (ed.), "Remington's Pharmaceutical Sciences," 18th edition, Mack Publishing Co., Easton, Pa., 1990; and Remington, "The Science and Practice of Pharmacy," 20th edition, Mack Publishing, 2000).

As used herein, administration "in conjunction" includes simultaneous administration and/or administration at different times. Administration in conjunction also encompasses administration as a co-formulation (e.g., IL-15 and a second compound(s) known to be useful for treating acute myocardial infarction and/or stroke) or administration as separate compositions. As used herein, administration in conjunction is meant to encompass any circumstance wherein IL-15 and another therapeutic agent, such as a compound known to be useful for the treatment of acute myocardial infarction, is administered to subject, which can occur simultaneously and/or separately. IL-15 and any other compound can be administered at different dosing frequencies or intervals via the same route of administration or different routes of administration. Such compounds are suitably present in combination in amounts that are effective for the purpose intended.

The phrase "additional agent derived from a bone marrow extract" as used herein, refers to a compound typically present in a bone marrow extract. In some embodiments, the additional agent is enriched or purified from a bone marrow extract. In other embodiments, the additional agent is a protein produced recombinantly or synthetically.

The terms "purified" and "isolated" as used herein refer to molecules (e.g., proteins) that are removed from their natural environment. Substantially "purified" molecules are at least 60% free, preferably at least 75% free, and more preferably at least 90% free from other components with which they are naturally associated.

DETAILED DESCRIPTION

The present disclosure relates generally to the field of cardiovascular diseases. In particular, the present disclosure relates to methods and compositions for treating cardiovascular diseases by administration of a cytokine alone, or in conjunction with other therapeutic agents.

Treatment Methods

This disclosure generally relates to methods of treating ischemic heart disease in a mammalian subject. The term ischemic heart disease encompasses coronary heart disease, coronary artery disease, acute coronary syndrome, angina pectoris, myocardial infarction, ischemic cardiomyopathy, and congestive heart failure. The disclosure also relates to methods of treating ischemic cardiovascular disease in a mammalian subject. The term ischemic cardiovascular disease encompasses coronary heart disease, coronary artery disease, acute coronary syndrome, angina pectoris, myocardial infarction, ischemic cardiomyopathy, congestive heart failure, and stroke.

In one embodiment the methods relate to treating a subject suspected of having a myocardial infarction and/or stroke comprising administering an effective amount of IL-15 to a subject in need of such treatment. In some embodiments, the myocaridal infarction is an acute myocardial infarction (AMI). In some embodiments, the IL-15 is administered as part of a composition further comprising an additional agent. In some embodiments, the additional agent comprises at least one factor derived from a bone marrow extract. In some embodiments, stroke is an acute neurocerebral accident. The criteria for diagnosing and evaluating subjects for AMI are known in the art, for example, in Braunwald, 2001, supra; Crawford, 2003, supra; "Myocardial Infarction Redefined—A Consensus Document of The Joint European Society of Cardiology/American College of Cardiology Committee for redefinition of Myocardial Infarction" J American College of Cardiology, 36: 959-969, 2000; American Heart Association Guidelines for Acute Myocardial Infarction; and The American College of Cardiology Guidelines for Acute Myocardial Infarction.

Generally, by way of example and not limitation, a subject is suspected of having an AMI if the subject presents with one or more of the following symptoms: ischemic symptoms, such as by way of example, chest, epigastric, arm, wrist or jaw discomfort and/or pain; nausea; vomiting, weakness, dizziness, palpitations, cold perspiration, dyspnea, syncope, and/or diaphoresis. Symptoms of stroke may include but are not limited to numbness, weakness, difficulty speaking or swallowing, hearing loss, and combinations thereof. Diagnosis also generally involves assessment of various diagnostic indicators and a clinical examination. Examples of diagnostic indicators include, but are not limited to rise and fall in biochemical markers indicative of myocardial necrosis, such as for example but not limited to, troponin and myocardial muscle creatinine kinase enzyme (CK-MB), development of pathologic Q waves on an electrocardiogram (ECG) and/or ST segment elevation or depression on an ECG. Generally, combinations of one or more symptoms and one or more diagnostic indicators are used in the evaluation of the patient. Generally, criteria for an established diagnosis of acute myocardial infarction include, but are not limited to, development of new pathologic Q waves on serial ECGs, normalization of biochemical markers of myocardial necrosis, and/or pathological findings of a healed or healing myocardial infarction. Criteria for establishment of stroke include neurologic physical examination and imaging, including but not limited to heat CT or MRI with or without perfusion imaging.

The management of patients presenting with suspected acute myocardial infarction will generally vary depending on whether the patient's ECG shows an ST elevation or an ST, depression (see, e.g., Ryan et al. AAC/AHA Guidelines for the Management of Patients with Acute Myocardial Infarction, J American College of Cardiology, 1999). Generally, patients who have an ST elevation on ECG will be administered thrombolytics or sent for PCI if available at the facility where the patient has been admitted. Accordingly, in yet another embodiment the method relates to treating an ST elevated acute myocardial infarction in a subject, comprising administering IL-15 to a subject in need of such treatment (e.g., myocardial infarction patient). In some embodiments, the IL-15 is administered as part of a composition further comprising an additional agent. In some embodiments, the additional agent comprises at least one factor derived from a bone marrow extract.

Treatment of patients with stroke will generally depend on the time of presentation after initial onset of symptoms. Patients are generally treated with thrombolytic therapy or interventional procedure on the infarct-related artery, in addition to more conservative therapies. Accordingly, in yet another embodiment the method relates to treating a stroke in a subject, comprising administering IL-15 to a subject in need of such treatment (e.g., stroke patient). In some embodiments, the IL-15 is administered as part of a composition further comprising an additional agent. In some embodiments, the additional agent comprises at least one factor derived from a bone marrow extract.

IL-15 acts as a cardioprotective and cardioneuroprotective agent based on its ability to rescue cardiomyocytes and neurons from hypoxia-induced cell death. Efficacy of the treatment can be evaluated by medical personnel based on a variety of standard tests. Examples of such techniques include, but are not limited to, measurement of biochemical markers indicative of myocardial or neuronal necrosis, such as for example, troponin and myocardial muscle creatinine kinase enzyme (CK-NM), Q waves on an electrocardiogram (ECG); ST segment on an ECG; reduction in infarction size, and/or reduction in reperfusion injury. Amelioration of any one or more symptoms of AMI or stoke is indicative of the efficacy of the treatment.

In another embodiment IL-15 is used in the manufacture of a medicament for treating myocardial infarction or stroke in a subject in need of such treatment or for treating a subject suspected of having a myocardial infarction or stoke. The medicament may be administered by methods and dosages exemplified herein.

Pharmaceutical Compositions

IL-15 used in this disclosure may be synthetically or recombinantly produced or isolated from natural sources by methods known in the art. Preferably the mature form of human IL-15 is used (SEQ ID NO:1). However, IL-15 variants having from one to 10 conservative substitutions as compared to wild type IL-15 are also suitable for use in embodiments of the present disclosure. Conservative substitutions are known to those of skill in the art. Criteria for conservative substitutions include, but are not limited to, similar charge, polarity, hydrophobicity, stearic confirmation and bulkiness.

The IL-15 compositions of the present disclosure can further comprise pharmaceutically acceptable carriers, excipients, or stabilizers, in the form of lyophilized formulations or aqueous solutions. Acceptable carriers, excipients, or stabilizers are nontoxic to recipients at the dosages and concentrations, and may comprise buffers such as phosphate, citrate, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium or acetate; metal complexes (e.g. Zn-protein complexes); and/or non-ionic surfactants such as TWEEN™, PLURONICS™ or polyethylene glycol (PEG).

IL-15 or a pharmaceutically acceptable formulations thereof may be formulated for parenteral administration (e.g., intravenous, intra-arterial, subcutaneous, or intramuscular injection). By way of example, an intravenous formulation may be used in the methods described herein comprises saline and about 0.05% polysorbate AB (e.g., TWEEN-80). For parenteral administration, such as intravenous administration, a dose of IL-15 may be combined with a sterile aqueous solution, which is preferably isotonic with the blood of the patient. Such a formulation may be prepared by dissolving a solid active ingredient in water containing physiologically-compatible substances such as sodium chloride, glycine, and the like, and having a buffered pH compatible with physiological conditions so as to produce an aqueous solution, and then rendering the solution sterile by methods known in the art. The formulations may be present in unit or multi-dose containers, such as sealed ampules or vials.

EXAMPLES

The present disclosure is described in further detail in the following examples, which are not in any way intended to limit the scope of the disclosure as claimed. The attached FIGURES are meant to be considered as integral parts of the specification and description of the disclosure. The following examples are offered to illustrate, but not to limit the claimed disclosure.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); ND (not done); NA (not applicable); rpm (revolutions per minute); $H_2O$ (water); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); PCR (polymerase chain reaction); and RT-PCR (reverse transcription PCR).

Additional abbreviations include: BMC (bone marrow cell); CM (cardiomyocyte); HPFs (high power fields); H/R (hypoxia/reperfusion); Hx (hypoxia); IL-15 (interleukin-15); MI (myocardial infarction); and Nx (normoxia).

Example 1

Cardioprotective Effect Of Interleukin-15 (Il-15)

Injection of exogenous bone marrow cell (BMC) extract following experimentally induced myocardial infarction was previously shown to provide functional improvement (Yeshiazarians et al., Molec Ther, 17:1250-1256, 2009). Subsequently, IL-15 was identified as an overexpressed factor by using RAYBIO® Mouse Cytokine Antibody Array (96 cytokines). Changes in IL-15 levels in mouse hearts post-MI compared to control non-infarcted hearts were also noted. This example describes the identification of IL-15 as a cardioprotective component of BMC extracts, and the detection of IL-15 receptors (e.g., IL-15Ralpha, IL-2Rbeta and IL-2Rgamma) on cardiomyocytes.

Figure 1B:
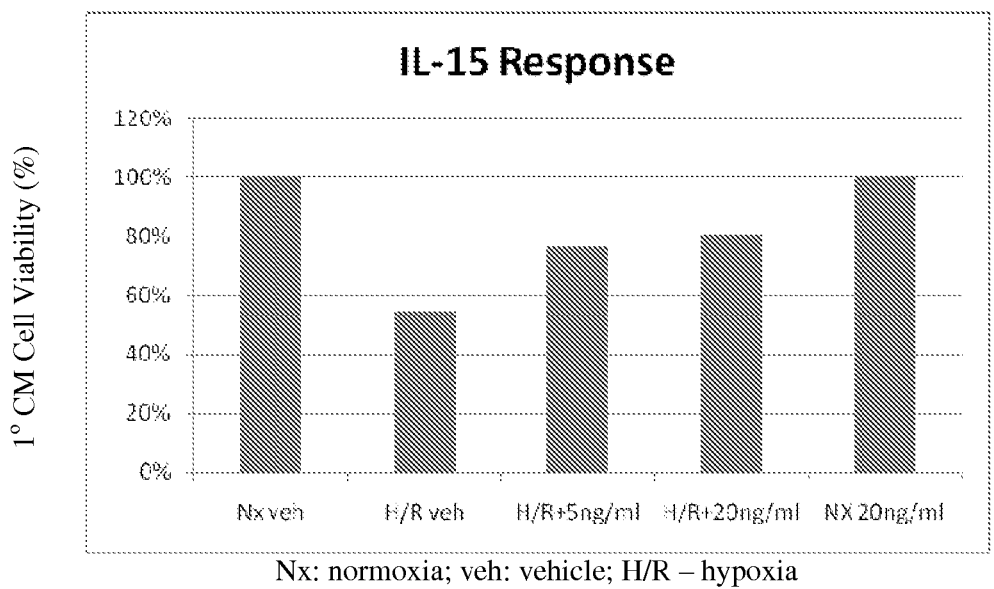
Figure 1C:
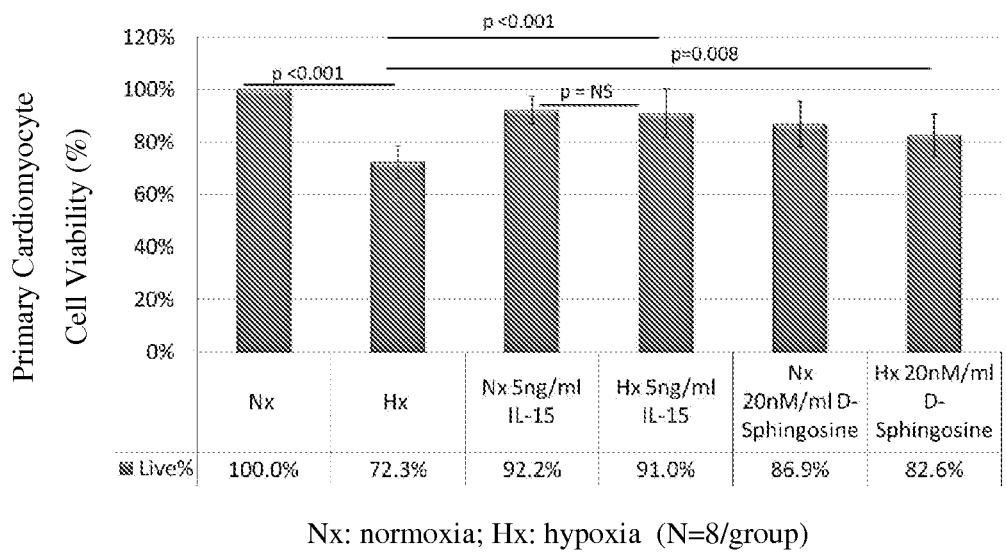
FIG. 1C illustrates the protective effect of IL-15 on hypoxia-induced death of primary adult mouse ventricular cardiomyocytes. The positive control D-sphingosine (20 mM/ml) also resulted in a significant increase in cell survival.

Two different cardiomyocyte (CM) cell sources were tested: HL-1 mouse atrial cell line; and primary CMs harvested from adult mice. The HL-1 cell line was established from an AT-1 subcutaneous tumor excised from an adult female inbred C57BLy6J mouse (Claycomb et al., Proc Natl Acad Sci USA, 95:2979-2984, 1998). To induce apoptosis, the cells were incubated in MEM low glucose (1 g/L) for 24 hrs. Cells were then subjected to hypoxia (0.5% $O_2$) (HL-1: 5-6 hrs; adult CM: 3 hrs), and allowed to recover in reperfusion phase (21% $O_2$) in the presence or absence of IL-15 (HL-1: 18-24 hrs; adult CM: 16-18 hrs). Recombinant mouse IL-15 was obtained from Invitrogen (Catalog No. PMC0154). HL-1 cell viability was evaluated using a MTT proliferation assay. Live cells contain active mitochondrial dehydrogenase that metabolizes the MTT dye to yield a purple formazan, whose absorbance is quantifiably read using a spectrophotometer. Primary CM cell viability was evaluated using Trypan blue vital staining. As shown in FIG. 1A-1B, the addition of IL-15 "rescues" cardiomyocytes from hypoxia-induced apoptosis.

Western blots were done to examine IL-15 receptor expression by cardiomyocytes. Total cell proteins and membrane proteins from whole heart were fractionated by SDS-PAGE. IL-15Ralpha, IL-2Rbeta (61 kDa) and IL-2Rgamma (65 kDa) were detected in the membrane protein fraction using a rabbit polyclonal anti-IL2 receptor beta antibody (Abcam, Catalog No. ab61195) and a rabbit polyclonal anti-IL2 receptor gamma antibody (Abcam, Catalog No. ab50258), respectively.

Example 2

Treatment of Myocardial Infarction (MI) with Interleukin-15 (Il-15)

This example describes methods for decreasing infarct size after MI by administration of a composition comprising an effective amount of IL-15.

Animals and Study Groups.

Male C57BL/6J (10-12 weeks old) mice are used for all experiments and handled according to the guidelines of the Institutional Animal Care and Use Committee.

MI and Echocardiography.

MI is surgically induced as previously described (Springer et al., Am J Physiol Heart Circ Physiol, 289:H1307-H1314, 2005). Briefly, infarction is induced by permanent ligation of the left anterior descending artery at ~50% of the length of the heart from the anterior-inferior edge of the left atrium to the apex. Echocardiography is accomplished under isoflurane anesthesia with the use of a Vevo660 (VisualSonics, Toronto, Canada) equipped with a 30-MHz transducer (Takagawa et al., J Appl Physiol, 102:2104-2111, 2007; and Zhang et al., Am j Physiol Heart Circ Physiol, 292:H1187-H1192, 2007). Echocardiograms are obtained at baseline, 2 days post-MI (before injection), and at day 28 post-MI. Left ventricular ejection fraction, end-systolic volume, end-diastolic volume, and wall thickness are measured. Wall thickness is measured at the apical anterior wall (infarct wall thickness) and at the mid-anterior segment (peri-infarct wall thickness) separately on the parasternal long-axis view; posterior wall thickness is obtained at the papillary muscle level. Three cycles are measured for each assessment and the average values are obtained. The analyses of the echocardiography images are performed by two blinded reviewers.

Ultrasound-Guided Injections.

Animals receive ultrasound-guided injection of a composition comprising isolated IL-15, or vehicle alone into myocardium as previously described (Springer et al., 2005, supra). Each heart is injected at day 3 post-MI with 10 µl of an isotonic solution containing IL-15, or 10 µl of the isotonic vehicle (e.g., HBSS), divided into two 5-µl injections into the anterior wall. Animals that are judged to be non-optimally injected due to poor injection into the left ventricular cavity are removed from the study.

Tissue Analysis.

Tissue is analyzed by two blinded reviewers and the average of the two analyses is reported at day 28 for the animals described. Infarct size is measured histologically as previously described (Takagawa, 2007, supra). To assess for histologic changes early after each therapy, additional animals are included and sacrificed at day 6 post-MI (i.e., day 3 post-therapy). Briefly, sections from the mid-ventricular level are examined for blood vessel density and arteriole count using antibodies to CD31 (Biocare, Concord, Calif.) and α-smooth muscle actin (Sigma-Aldrich, St Louis, Mo.). Blood vessel density is analyzed using ImagePro software (MediaCybernetics, Bethesda, Md.) to detect the area of CD31 staining in the infarct zone, the BZ, and the remote myocardium. Arterioles defined as CD31+ vessels with an α-smooth muscle actin coating are manually counted in each region. Capillaries are also quantified manually at day 28 using BS1 isolectin B4 staining.

Sections from the mid-ventricular level are examined for the presence of CMs that were undergoing apoptosis or were in cell cycle. Apoptosis is detected by two complementary methods: the colocalization of antibody staining for cardiac troponin-I (Abcam, Cambridge, Mass.) and TUNEL staining (ApopTag; Chemicon, Temecula, Calif.) within the same cell, and the colocalization of antibody staining for activated caspase-3 (BD Pharmingen, San Jose, Calif.) and for cardiac troponin-I within the same cell. CMs in cell cycle are detected using two complementary methods: co-staining for troponin-I and Ki67 (antibody from DAKO, Carpinteria, Calif.) within the same cell, and co-staining for troponin-I and proliferating cell nuclear antigen (antibody from Biocare) within the same cell. These apoptotic and cycling CMs are quantified by blinded reviewers counting the number of positive cells in five high power fields (HPFs) in the infarct zone, BZ, and the remote myocardium.

Early Time-Point (Day 6 Post-MI) Tissue Analysis

Tissue Preparation.

Hearts are arrested in diastole with intravenous injection of saturated potassium chloride, before removal. The hearts are then perfused with 10% formalin injected into the aorta. When successful fixation is achieved, the hearts are immersed in 10% formalin for 12 hours. They are then transferred to 80% alcohol and then paraffin embedded. Paraffin embedded sections from the mid-papillary level of the left ventricle are examined as follows.

Histological Detection of Capillaries and Arterioles.

Paraffin-embedded tissues are deparaffinized in changes of xylene and rehydrated in decreasing concentrations of ethanol. Sections are treated with trypsin. After rinsing in distilled water, the sections are treated with a peroxidase solution (Biocare). The sections are then rinsed with Tris Buffered Solution (TBS) before blocking with a universal block (Biocare). A primary rat antibody against CD31 (Biocare, 1:25 dilution) is applied to the sections for 2 hours at room temperature. The slides are then rinsed with TBS. A Rat Detection Kit (Biocare) is used to detect the rat-anti-CD31 antibody. The stain is developed using 3,3'-diaminobenzidine (DAB). A denaturing solution (Biocare) is applied for 3 min to stop any reaction from the CD31 stain, before proceeding to stain for smooth muscle actin. After washing the sections in TBS, a mouse primary antibody against alpha-smooth musclactin (Sigma-Aldrich, St. Louis, Mo.; 1:100 dilution) is applied for one hour at room temperature. The tissues are washed with TBS and a Mouse on Mouse Polymer (Biocare) conjugated to alkaline phosphatase is applied to the sections for 20 min at room temperature. The sections are washed in TBS again, and the stain is developed using a Ferangi Blue Chromogen Kit (Biocare). The tissues are then dehydrated in increasing concentrations of ethanol, and three changes of xylene. The negative controls are treated using the same methodology, omitting the primary antibody, and replacing it with the diluent. Low power photomicrographs are taken of three regions: Infarct Zone (IZ), Border Zone (BZ) and Remote Myocardium (RM). These images are analyzed using Image Pro software. The software is taught to recognize brown CD31+ staining using the Magic Wand tool and the recognition parameters are modified for each image until representative selection is achieved. A percentage vessel area is obtained for each of the three regions. The absolute number of arterioles is counted manually in five high power fields within each region.

Histological Detection of Ki67+ Cardiomyocytes.

Paraffin embedded tissues are deparaffinized in changes of xylene and rehydrated in decreasing concentrations of ethanol. Antigen retrieval is then performed in a citrate buffer solution (Biocare). Sections are then rinsed with distilled water, and treated with peroxidase, TBS, and universal block as described above. A primary rat monoclonal antibody against Ki67 (DAKO, Capinteria, Calif.; 1:10 dilution) is applied to the sections for 2 hours at room temperature. After washing with TBS, a Rat Detection Kit (Biocare) is used to detect the primary antibody. The stain is developed using DAB. The sections are then denatured for 5 min using denaturing solution. After blocking with a universal block (Biocare) for 20 min, a mouse anti-Troponin-I antibody (Abcam, Cambridge, Mass.) is diluted in TBS and applied to sections for 1.5 hours at room temperature. Sections are rinsed with TBS and a Mouse on Mouse Polymer (Biocare), conjugated to alkaline phosphatase, is applied to sections for 20 min After rinsing sections, the stain is developed using Vulcan Fast Red Chromogen and counterstained with CAT hematoxylin (both from Biocare). The number of Ki67+ cardiomyocytes is counted in five high power fields per region (IZ, BZ and RM) by two blinded counters. These numbers are then averaged. A positive Ki67+ cardiomyocyte is defined as one with a positively stained nucleus, morphologically resembling a cardiomyocyte nucleus completely surrounded by troponin staining.

Histological Detection of PCNA+Cardiomyocytes.

Paraffin embedded tissues are deparaffinized, rehydrated, subjected to antigen retrieval, treated with peroxidase, rinsed with TBS, and blocked with a universal block as described above for Ki67 staining. A primary mouse antibody against PCNA (Biocare, 1:200 dilution) is applied to the sections for 2 hrs at room temperature. After washing with TBS, a Mouse on Mouse polymer conjugated to alkaline phosphatase (Biocare) is used to detect the primary antibody. The stain is developed using Ferangi Blue. The sections are then washed with distilled water. After blocking with universal block, troponin-I staining using Vulcan Fast Red is carried out as described above for Ki67 staining. The number of PCNA+ cardiomyocytes is counted in five high power fields per region (IZ, BZ and RM). These numbers are then averaged. A positive PCNA+ cardiomyocyte is defined as a one with a positively stained nucleus, morphologically resembling a cardiomyocyte nucleus completely surrounded by troponin staining.

Histological Detection of Apoptotic Cardiomyocytes.

Five micron sections at mid-papillary level are taken from paraffin-embedded hearts harvested 6 days post-MI. Apoptotic cardiomyoctes are identified using two methods: TUNEL co-stained for troponin-I (TnI) and active caspase-3 co-stained with TnI. TUNEL staining is performed with APOPTAG® Plus Peroxidase In Situ Apoptosis Detection Kit (Chemicon, Temecula, Calif.) according to manufacturer's protocol, except the terminal deoxynucleotidyl transferase is diluted to 50% in the supplied reaction buffer. After color development in DAB, denature solution is applied (Biocare) to prevent cross reaction with the following TnI staining. The slides are treated with Rodent Block M (Biocare) to block endogenous IgG, and then incubated for 1.5 hr with TnI primary antibody (Abcam, 1:50) dissolved in TBS. For detection of TnI primary antibodies, mouse-on-mouse alkaline phosphatase polymer (Biocare) is applied to the slides for 25 min at room temperature, followed by color development in Vulcan Fast Red. Finally, slides are counterstained with hematoxylin. TUNEL-positive cardiomyocytes are defined by the presence of both DAB nuclear staining and cardiomyocyte nucleus morphology that is completely surrounded by troponin-I staining. For fluorescent detection of active caspase-3, sections are deparaffinized and antigen-retrieved in Rodent Decloaker (Biocare, Concord, Calif.) by 20 min of microwave heating. The slides are treated with Rodent Block M to block endogenous IgG, followed by overnight 4° C. incubation in staining buffer containing both rabbit anti-mouse cleaved-caspase-3 antibody (BD Pharmingen, San Jose, Calif., 1:100) and mouse anti-mouse TnI antibody (Abcam, 1:50). The slides are then incubated in secondary goat anti-rabbit IgG conjugated to ALEXA FLUOR® 488 and secondary goat anti-mouse IgG conjugated to ALEXA FLUOR® 546 (Invitrogen, Carlsbad, Calif.), followed by preservation in VECTASHIELD® mounting medium containing DAPI (Vector Laboratories, Burlingame, Calif.). High power field pictures at border zone are taken for quantification of caspase-positive cardiomyocytes, defined by presence of caspase-3 signal completely enclosed in cells with TnI staining.

Late Time-Point (Day 28 Post-MI) Tissue Analysis

Tissue Preparation.

Hearts are arrested in diastole with intravenous injection of saturated potassium chloride, before removal. They are then frozen in OCT for tissue sectioning using a cryostat.

Immunofluorescence and Lectin Staining.

Frozen tissue sections are fixed with 1.5% formaldehyde for 15 min and blocked with antibody buffer consisting of 2% normal goat serum, 0.3% Triton X-100 and 0.02% sodium azide in PBS for 30 min. When mouse primary antibodies are to be used, an additional blocking step is performed in which sections are incubated for 30 min in a mouse-on-mouse blocking solution based on the method of Lu and Partridge, which utilizes 0.2 mg/ml AffiniPure Fab fragment goat anti-mouse IgG (H+ L), 0.2 mg/ml AffiniPure Fab fragment goat anti-rat IgG (H+ L), and 0.2 mg/ml ChromePure goat IgG, Fc fragment (all from Jackson ImmunoResearch Laboratories, West Grove, Pa.) in antibody buffer. The slides are incubated for 1 hour at room temperature in antibody buffer containing individual or multiple primary antibodies as follows: a rat monoclonal antibody against mouse F4/80 (BD Pharmingen, San Diego, Calif.; 1:100 dilution), a rabbit polyclonal antibody against human cardiac troponin T that cross-reacts with mouse cardiac troponin T (ab10224, Abcam, Cambridge, Mass.; 1:200), and mouse monoclonal antibodies against the following markers: α-smooth muscle actin (clone 1A4; ICN Biomedicals, Aurora, Ohio; 1:400 dilution), cardiac troponin I [4C2] (ab10231, Abcam; 1:200), the pericyte marker NG2 (clone 132.38; Chemicon, Temecula, Calif.; 1:200), CD45 (BD, Franklin Lakes, N.J.; 1:500), and human NuMA (nuclear mitotic apparatus antigen, Abcam, 1:50). The troponin T antibody is initially used for cardiomyocyte staining, but tissue autofluorescence is sufficient for visualization of cardiomyocytes for most needs. Sections are rinsed in antibody buffer, and then incubated for 1 hour in the appropriate secondary anti-IgG conjugated to ALEXA FLUOR or 350, ALEXA FLUOR 488, ALEXA FLUOR 546, or ALEXA FLUOR 660 (Invitrogen/Molecular Probes, Carlsbad, Calif., 1:200 dilution), with Hoechst 33258 nuclear dye at 0.1 µg/ml when appropriate. For day 28 capillary staining, sections are stained as described above but biotinylated BS-1 isolectin B4 from *Griffonia simplicifolia* is used in place of the primary antibody (Sigma-Aldrich, 1:100 dilution), and streptavidin conjugated to ALEXA FLUOR 647 (Invitrogen/Molecular Probes, 1:100 dilution) is used for detection. The slides are then rinsed, mounted, and viewed with a Nikon E800 fluorescence microscope using Openlab software (Improvision, Lexington, Mass.). Negative staining controls lacking primary antibody are performed in parallel.

Manual Quantitation of Blood.

Capillaries are recognized by BS1 isolectin B4 staining of endothelial cells in one color, and arterioles are detected by α-smooth muscle actin immunofluorescence in a different color. Digital photomicrographs of stained vessels are obtained with Openlab software. Capillary segment density and arteriole density indices are calculated by counting the number of distinct vessel segments in high-magnification fields. Vessel area density and vessel length density indices are calculated as follows. A pattern consisting of repeating sine waves in a third color is imported into Openlab as a new layer, merged with each capillary photo, and the number of intersections of vessels with the pattern was counted. Vessel area density index is defined as the total number of intersections of capillaries and overlay pattern. Vessel length density is defined as the number of intersections of capillary centerlines and overlay pattern. To control for artificially decreased numbers due to rips and gaps in the tissue, the number of sine wave peaks and troughs that occurred within tissue is counted for each field, and all vessel density indices are normalized to the number of tissue sine wave peaks/troughs to yield corrected indices for each field. All counts are performed by an investigator blinded to the identity of the sections.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

We claim:

1. A method for the treatment of ischemic cardiovascular disease, comprising: administering a composition comprising isolated interleukin-15 (IL-15) to a patient in need thereof.

2. The method of claim 1, wherein the ischemic cardiovascular disease is myocardial infarction (MI).

3. The method of claim 2, wherein said composition comprises said IL-15 in an amount effective to reduce scarring following said myocardial infarction.

4. The method of claim 2, wherein said composition comprises said IL-15 in an amount effective to increase left ventricular ejection fraction following said myocardial infarction.

5. The method of claim 2, wherein said composition comprises said IL-15 in an amount effective to enhance mycardial remodeling following said myocardial infarction.

6. The method of claim 2, further comprising administering to the patient an agent used in the routine treatment of myocardial infarction, either sequentially or simultaneously with said composition comprising IL-15.

7. The method of claim 6, wherein the agent used in the routine treatment of myocardial infarction is selected from the group consisting of thrombolytic agents, glycoprotein IIb-IIIa, other platelet inhibitors, calcium channel blockers, anti-arrhythmics, heparin, nitrates, beta-blockers, angiotensin receptor blockers, and angiotensin converting enzyme inhibitors.

8. The method of claim 1, wherein the ischemic cardiovascular disease is stroke.

9. The method of claim 8, wherein said composition comprises said IL-15 in an amount effective to decrease negative consequences of the stroke.

10. The method of claim 8, further comprising administering to the patient an agent used in the routine treatment of stroke, either sequentially or simultaneously with said composition comprising IL-15.

11. The method of claim 10, wherein the agent used in the routine treatment of stroke is selected from the group consisting of thrombolytic agents, glycoprotein IIb-IIIa, other platelet inhibitors, calcium channel blockers, anti-arrhythmics, heparin, nitrates, beta-blockers, angiotensin receptor blockers, and angiotensin converting enzyme inhibitors.

12. A method of protecting cells from hypoxia-induced cell death, comprising contacting said cells that have been exposed to hypoxic conditions with a composition comprising isolated IL-15 so as to increase viability of said cells, wherein said cells are cardiomyocytes or neurons.

13. The method of claim 12, wherein said contacting is in vitro or ex vivo.

14. The method of claim 13, wherein said cells are cardiomyocytes that are part of a mammalian heart harvested for transplantation.

15. The method of claim 13, wherein said cells are neurons that are part of a mammalian brain or spinal cord harvested for transplantation.

16. The method of claim 12, wherein said contacting is in vivo.

17. The method of claim 16, wherein said hypoxic conditions comprise a myocardial infarction.

18. The method of claim 17, wherein said contacting comprises administration of said composition comprising IL-15 to a mammalian subject by intravenous injection or by ultrasound-guided injection proximal to said myocardial infarct.

19. The method of claim 16, wherein said hypoxic conditions comprise a stroke.

20. The method of claim 19, wherein said contacting comprises administration of said composition comprising IL-15 to a mammalian subject by intravenous injection or by ultrasound-guided injection proximal to said stroke.

* * * * *